United States Patent [19]
Gjunter

[11] Patent Number: 5,986,169
[45] Date of Patent: Nov. 16, 1999

[54] POROUS NICKEL-TITANIUM ALLOY ARTICLE

[75] Inventor: Victor Gjunter, Tomsk, Russian Federation

[73] Assignee: Biorthex Inc., Canada

[21] Appl. No.: 09/001,496

[22] Filed: Dec. 31, 1997

[51] Int. Cl.[6] .................................................. A61F 2/28
[52] U.S. Cl. .............................................. 623/16; 623/18
[58] Field of Search ................................ 623/16, 11, 66, 623/18

[56] References Cited

U.S. PATENT DOCUMENTS

| | | | |
|---|---|---|---|
| 3,855,638 | 12/1974 | Pilliar | 623/16 |
| 3,906,550 | 9/1975 | Rostoker | 623/20 |
| 4,542,539 | 9/1985 | Rowe | 623/16 |
| 4,693,721 | 9/1987 | Ducheyne | 623/16 |
| 5,171,281 | 12/1992 | Parsons | 623/17 |
| 5,306,309 | 4/1994 | Wagner | 623/17 |
| 5,458,643 | 10/1995 | Oka | 623/18 |
| 5,665,119 | 9/1997 | Koller | 623/16 |

FOREIGN PATENT DOCUMENTS 1381764   5/1982   Russian Federation.

*Primary Examiner*—Michael J. Milano
*Attorney, Agent, or Firm*—Bachman & LaPointe, P.C.

[57] ABSTRACT

A porous article of a nickel-titanium alloy, said article having a porosity of 8 to 90% and said porosity being defined by a network of interconnected passageways extending throughout said member, said network exhibiting a permeability of fluid material effective to permit complete migration of the fluid material throughout said network, said permeability being isotropic, and said member being elastically deformable; the porous article is useful as a biomedical implant and in other non-medical applications including the working element of cryogenic surgical instruments.

12 Claims, 3 Drawing Sheets

POROUS NICKEL-TITANIUM ALLOY ARTICLE

BACKGROUND OF THE INVENTION

1. Field of the Invention

This invention relates to a porous article of a nickel-titanium alloy having medical and non-medical applications.

2. Description of Prior Art

Nickel-titanium alloys are known shape memory alloys which have been proposed for use in various environments including robotics and in memory devices of medical implants.

Soviet Union Patent Specification 1,381,764 dated 1982 proposes implants for facial reconstruction fabricated from a nickel-titanium alloy having a porosity of 8–60%, but the disclosure is very limited and there has been no commercial development of the material described.

U.S. Pat. Nos. 4,206,516; 4,101,984; 4,017,911 and 3,855,638 all describe composite implants having a solid substrate with a thin porous surface coating. U.S. Pat. No. 3,852,045 describes a bone implant element of porous structure in which the pores are developed by means of solid expendable void former elements which are arranged in a selected spatial pattern in a form cavity; metallic particles are packed about the void former elements, the mix is densified, the void former elements are removed, such as by vaporization and the metallic particles are sintered.

The search continues for materials suitable for fabricating medical implants, and for materials of improved physical characteristics.

SUMMARY OF THE INVENTION

It is an object of this invention to provide a porous article of a nickel-titanium alloy, useful in biomedical and other applications.

In accordance with the invention there is provided a porous article of a nickel-titanium alloy, said article having a porosity of 8 to 90% and said porosity being defined by a network of interconnected passageways extending throughout said member, said network exhibiting a permeability for fluid material effective to permit complete migration of the fluid material throughout said network, said permeability being isotropic and said member being elastically deformable.

DESCRIPTION OF PREFERRED EMBODIMENTS i) Porous Alloy Article

The porous alloy article of the invention has a porosity of 8 to 90%.

Preferably the porosity is at least 40% and preferably not more than 80%.

Preferably the permeability is derived from capilliarity in the network of passageways which define the porosity.

This capilliarity may be produced in the article by inclusion therein of a large number of pores of fine size which interconnect to produce capilliary passages.

Capilliarity is advantageous in that it promotes migration of a desired fluid material into the network of passageways, and retention of the fluid material in the network, without the need to apply external hydraulic forces.

In general the network has a coefficient of permeability of $2 \times 10^{-13}$ to $2 \times 10^{-5}$, and the permeability is isotropic.

The capilliarity and the isotropic character are, in particular, achieved when the network defining the porosity comprises pores of different pore size, the pore size distribution being as follows:

| Pore Size in Microns | Quantity |
|---|---|
| $10^{-2}$–10 | 1–15% |
| $10^{-1}$–10 | 5–10% |
| 10–100 | 10–20% |
| 100–400 | 20–50% |
| 400–1000 | 10–50% |
| above 1000 | remainder to 100%. |

The porosity of a material affects its physio-mechanical qualities, for example, mechanical durability, corrosion resistance, super-elasticity and deformational cyclo-resistivity.

The porous article of the present invention permits a wide field of application of the article without modifying the biomechanical and biochemical compatibility.

The size of the pores, the directional penetrability and the coefficient of wettability for biological fluids, as well as factors such as differential hydraulic pressure in the saturated and unsaturated porous article, determine the speed and adequacy of penetration of the biological fluid into the porous article.

It may be expected that an optimal pore size will provide permeability to the fluid and effective contact for bonding of components in the fluid with the interior pore surfaces of the article; the area of these surfaces depends on the pore sizes and the pore size distribution.

If the pore size is decreased the permeability changes unpredictably, since, on the one hand, the hydraulic resistance increases, while, on the other hand, the capillary effect appears at a certain low pore size, which capillary effect increases the permeability.

Pore size is also an important factor in tissue or biological aggregate growth. At least some of the pores need to be of a size to permit the development or growth of biological aggregates synthesized from the components of the fluid, for example, osteons, in the case of bone tissue.

Furthermore, if pore size is increased, the capillary effect decreases and the durability of the porous article also decreases. For each kind of live tissue there are optimum parameters of permeability, porosity and pore size distribution in the porous article for efficient operation of the porous article as an implant. The porous article of the invention functions well with a wide variety of live tissue and thus permits wide scope of use.

ii) Nickel-Titanium Alloy

The porous nickel-titanium alloy may suitably comprise 2 to 98%, by weight, titanium and 98 to 2%, by weight, nickel, to a total of 100%; preferably 40 to 60%, by weight, titanium and 60 to 40%, by weight, nickel, to a total of 100%.

Nickel-titanium alloy has significant advantages, as compared with other materials, in biomedical applications. In particular it displays a high level of inertness or biocompatibility, it has high mechanical durability thus providing longevity when employed in the fabrication of implants.

Live tissue has an elasticity which renders it resilient to permanent deformity when subjected to stress and vibrations. If material employed in an implant which contacts such tissue has different characteristics from the tissue it will not meet the requirement for biocompatibility in an implant and longevity will be short. The porous nickel-titanium alloy article of the invention is found to display mechanical behaviour very similar to that of live tissue, thus showing high biocompatibility iii) Article

Various porous articles may be fabricated in accordance with the invention.

One especially preferred class of articles of the invention is biomedical implants.

The porous alloy article may be fabricated as an implant or endoprosthesis for local or total replacement of a body part, for example, to correct birth defects or defects resulting from injury or disease.

Thus the porous alloy article may be fabricated as a spacer to replace a portion of shattered human bone and provide a bridge for connection of bone parts separated as a result of the shattering of the original bone.

Nickel-titanium alloys have a high level of biocompatibility with human tissue and the capillarity of the porous alloy article of the invention facilitates penetration of the article by human biological fluids under the force of capillary action. Thus biological fluid from the bone is drawn into the network of passageways of the contacting porous spacer, and the fluid migrates, under capillary action, throughout the network. Live tissue in the fluid grows within the pores of the network and adheres to the pore surfaces providing a chemical bonding or unification with the titanium-nickel alloy.

As the growth of tissue, for example, bone, is completed there is provided both a chemical bonding between the newly grown bone and the titanium nickel spacer, and a mechanical connection by the newly grown bone, to the separated bone parts which the spacer bridges.

The porous article may also be employed in other applications, for example, in a flame torch, where the porous article is fabricated as the torch head to provide a desired flame formation. A further application is as the working element of a surgical tool where the porous structure may act as a reservoir for a cooling liquid where the tool is employed in cryo-surgery. In the case where the working element is a cutting edge or tip, the cooling liquid in the porous structure may provide local freezing at a site where a cut or incision is being made, such as in wart removal.

Other applications of the porous article include detection devices for evaluation of air and gas environments, the air and gas environment being absorbed into and retained by the porous structure and later released under controlled conditions for evaluation.

The porous article may also be employed as a deformable filtering element for liquid and gas environments.

iv) Process

The porous article is produced with a controlled pore size distribution, as indicated above. In particular the porous article may be produced in accordance with the procedures described in the Russian publication "Shape Memory Alloys in Medicine", 1986, Thompsk University, p-205, Gunther V. et al, the teachings of which are incorporated herein by reference. In particular there is employed the so-called SBS method in which the alloy is produced by means of a layered combustion which exploits exothermic heat emitted during interaction of different elements, for example, metals. In this interaction a thermo-explosive regime takes place.

The porosity and porosity distribution are controlled by adjustment of the process parameters.

DESCRIPTION WITH REFERENCE TO DRAWINGS

Figure 1:
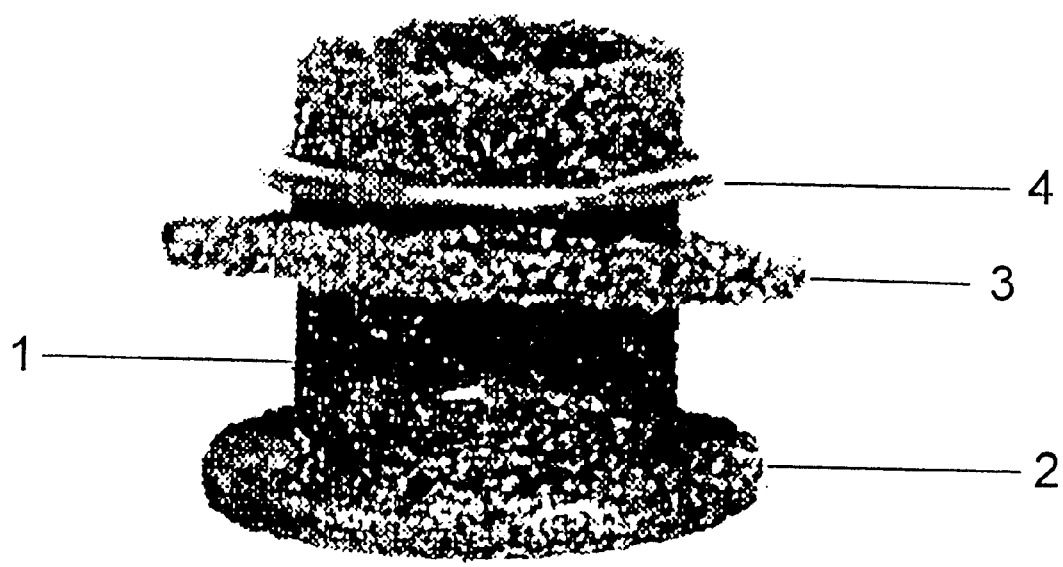
FIG. 1 shows a porous article of the invention as an implant.

With further reference to FIG. 1 a porous titanium-nickel alloy implant for through wounds of the liver comprises a sleeve 1, immobile limiting rib 2, removable limiting rib 3 and a retaining ring 4.

EXAMPLE 1

Implant Operation of a Through Wound of the Liver

Nickel-titanium alloy having a porosity of 65% was used, the alloy had an isotropic permeability of $2 \times 10^{-5}$ m$^2$ and a distribution of porosity according to the following pore sizes:

| | |
|---|---|
| $10^{-2}$–$10^{-1}$ microns | 5% |
| $10^{-1}$–10 | 10% |
| 10–100 | 20% |
| 100–400 | 50% |
| 400–1000 | 10% |
| over 1000 | 5% |

The composition was obtained by powder metallurgy method by means of a self-spreading or self-distributing high temperature synthesis regime of combustion with etching or picking afterwards. The porous material for the implant was made in a configuration of sleeve 1 (FIG. 1) having spaced apart limiting ribs 2, 3, one rib 2 being stationary and the other 3 being removable. The diameter of the sleeve 1 was 20 mm, length 30 mm, outside diameter of ribs 2, 3 was 25 mm. The removable rib 3 was mounted by means of a retaining ring 4.

The implant was utilized as follows:

After sterilization treatment, the animal (a dog) was anesthetized to allow access to the left lateral hemisphere of the liver by means of intermediate "lipothymy" using a sword-like appendix 15 cm long. Then, by using a cylindrical resector with an outside diameter of 22 mm, a perforation imitating a wounding channel was effected in the liver. By means of a sleeve-conductor, sleeve 1 was inserted into the wounding channel until the limiting stationary rib 2 abutted the liver, whereas the second end of the sleeve 1 remained outside the liver. Then, the removable rib 3 was mounted on this second end of the sleeve 1 to the limit where the liver became slightly depressed in such position. Then, the retaining ring 4 was affixed on the sleeve 1. During the operation, the length of resection lasted 5 seconds, installment and affixing of the implant lasted around 20 seconds; in this case, the bleeding of the liver happened only during resection and installation of implant. Blood loss was not more than 30 ml.

After installation of the implant, porous material was saturated with body liquid during the next 30–40 seconds, including the penetration of blood outside before it clotted inside the matrix of the pores. Blood loss during this operation was around 10–15 ml.

In the post-operation stage, during 12 months, the following occurrences were noticed: the dynamic of development and transformation of tissue on the border of the "parenchyma implant" including the development of a layer of fibrin (24 hours), its granulation (5–7 days), development and densening of collagen tissue in which vessels and liver lattice (6–12 months) had been developed. Thirty animals (dogs) were subjected to the described operation. Mortality rate in this group was 10% and was not implant-related, which is testimony of the high efficiency of the porous alloy material, which may be used for implantation of parachimose defects in human body organs.

EXAMPLE 2

Forming of Stump of the Eyeball

For this operation, porous titanium-nickel alloy with a degree of porosity of 90%, isotropic permeability of $2\times10^{-5}$ m$^2$, and the following distribution of pores according to sizes was used:

| | |
|---|---|
| $10^{-2}$–$10^{-1}$ microns | 1% |
| $10^{-1}$–10 | 5% |
| 10–100 | 10% |
| 100–400 | 20% |
| 400–1000 | 50% |
| over 1000 | 14%. |

The material was used with a cosmetic purpose and its effectiveness was determined according to the strength of bonding between the implant and the eyeball tissue, ability to resist resolving, and to maintain a pre-determined volume. The following procedure was used: first, the lab animal (dog) was subjected to a visceroeniculation and an implant was placed in the scleral glass/goblet after all vessel tissue had been removed; then, the scleras between the eye movement muscles were severed and used as patches to affix the implant with paired stitches.

Twenty animals were subjected to this operation; throughout the procedure, the animals did not have any complications in the implant-affected areas or elsewhere.

Figure 2:
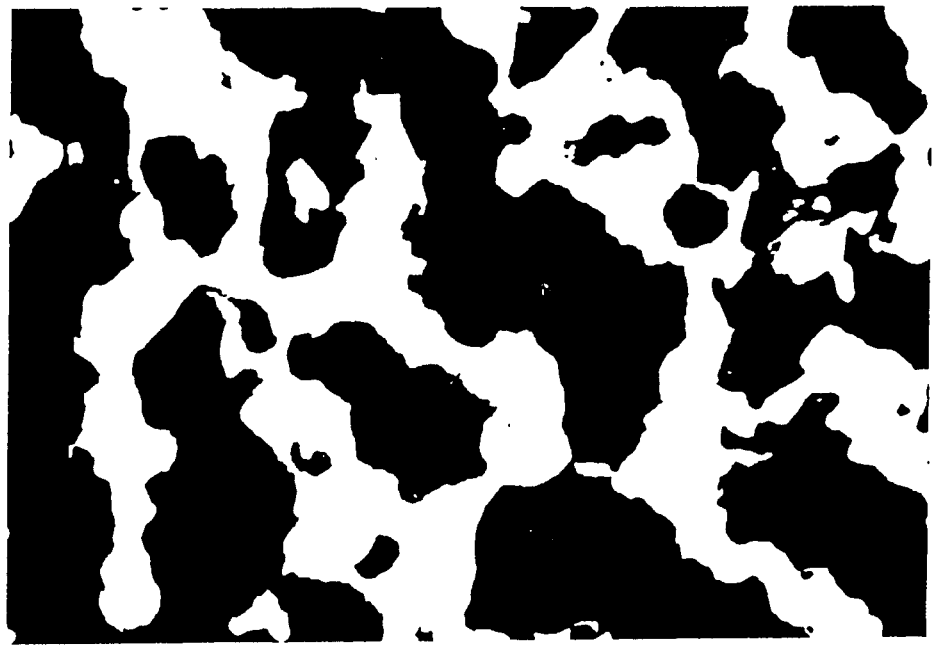
FIG. 2 shows the microstructure of an implant surface with in-grown tissue, 9 months after surgery.

Bonding of tissue in the implant pores and its transformation was studied by means of a micro-section after 7 days, and 3, 6, 9 and 12 months after the operation. FIG. 2 shows microstructure of the microsectional surface of implant showing the tissue filling 9 months after the operation. The results of the study show that a dense fibrose tissue is created inside the pores which remains stable thus creating a secure fixation and functionality of the implant.

EXAMPLE 3

Implant of Facial Skull Structure

During implantation of bone defects caused by osteoporosis (pathological disintegration of bone tissue), the most efficient titanium nickel alloy used was the one with a degree of porosity of 70–80%, isotropic permeability of $1.5\times10^{-5}$ m$^2$ and the following distribution of pore sizes:

| | |
|---|---|
| $10^{-2}$–$10^{-1}$ microns | 1% |
| $10^{-1}$–10 | 5% |
| 10–100 | 15% |
| 100–400 | 45% |
| 400–1000 | 30% |
| over 1000 | 4%. |

Figure 3:
FIG. 3 shows an implant for facial skull.

The material was obtained according to powder metallurgy method by means of self-spreading high temperature synthesis in a combustion regime. The material was tailored as a plate-like endoprothesis (FIG. 3) having a thickness from 0.5–1.0 mm obtained by the method of electro-erosion cutting of nuggets of porous titanium nickel alloy. Preparation of the endoprothesis for implantation consisted of sterilization by known standard procedures including dry-heat treatment and preservation in 96% alcohol.

EXAMPLE 4

The following shows the use of implant surgery for total defects of a nose: the object of the operation was the replacement of cartilage and bone areas of the nose bridge, which were lost during an illness or an accident. First, the remainder of the original bridge tissue was cleaned off and a hemostasis was performed. Then, the implant plates were tailored according to the shape of the defect (FIG. 3) by means of surgical scissors. The tailored implant was saturated in antibiotics and then placed by means of Quillion mirrors in the area of defects. Then, the tailored plate was configured along the edges of the defect and affixed with catgut stitches.

Additional fixation was provided by means of frontal loop wadding.

On the second day after the operation, the wadding was removed; after 4–5 days, antibiotic therapy was performed, and if necessary, laser therapy. The period of disability of the subject of the operation was 5–8 days.

Similar procedures for use of the porous material were used for replacement or implantation of other nose defects, frontal sinuses bone tissue and upper jaw tissue and lower wall of the eyeball cavity.

Results of the implants using porous titanium nickel alloy show significant advantages of the present material over known prior materials.

Material with a degree of porosity over 90% is impractical in view of its low mechanical durability.

We claim:

1. A porous article having a porous sintered powder body based on a nickel-titanium alloy, said article having a porosity of 8 to 90% and said porosity being defined by a network of interconnected passageways extending throughout said sintered powdered body, said network exhibiting a permeability for fluid material effective to permit complete migration of the fluid material throughout said network, said permeability arising from capilliarity in said network and said network having a distribution of pores as follows:

| Pore Size in Microns | Quantity |
|---|---|
| $10^{-2}$–$10^{-1}$ | 1–15% |
| $10^1$–10 | 5–10% |
| 10–100 | 10–20% |
| 100–400 | 20–50% |
| 400–1000 | 10–50% |
| above 1000 | remainder to 100%, | said article being elastically deformable.

2. A porous article according to claim 1, wherein said alloy is a biocompatible alloy.

3. A porous article according to claim 2, wherein said network is permeable to biological tissue in a biological fluid, and said network comprises pores of a size to permit growth of biological tissue therein.

4. A porous article according to claim 3, having a porosity of at least 40%.

5. A porous article according to claim 4, having a porosity of not more than 80%.

6. A porous article according to claim 5, having a coefficient of permeability of $2\times10^{-}$ to $2\times10^{-5}$.

7. A porous article according to claim 1, wherein said alloy comprises 2 to 98%, by weight, titanium and 98 to 2%, by weight, nickel, to a total of 100%.

8. A porous article according to claim 6, wherein said alloy comprises 40 to 60%, by weight, titanium and 60 to 40%, by weight, nickel to a total of 100%.

9. A porous article according to claim 1, in the form of a biomedical implant.

10. A porous article according to claim 8, in the form of a biomedical implant.

11. A porous article according to claim 1, wherein said permeability is isotropic.

12. A porous article according to claim 1, wherein said alloy comprises 40 to 60%, by weight, titanium and 60 to 40%, by weight, nickel, to a total of 100%.

* * * * *

UNITED STATES PATENT AND TRADEMARK OFFICE
CERTIFICATE OF CORRECTION

PATENT NO. : 5,986,169  
DATED : November 16, 1999  
INVENTOR(S) : Victor Gjunter Page 1 of 1

It is certified that error appears in the above-identified patent and that said Letters Patent is hereby corrected as shown below:

Column 6,  
Line 61, "2x10$^{---}$" should read -- 2x10$^{-13}$ --; and  
Line 67, after "nickel" a -- , -- should be inserted.

Signed and Sealed this

Fourteenth Day of January, 2003

JAMES E. ROGAN  
*Director of the United States Patent and Trademark Office*